United States Patent
Bardy et al.

(10) Patent No.: US 9,993,653 B2
(45) Date of Patent: **\*Jun. 12, 2018**

(54) APPARATUS AND METHOD FOR IDENTIFYING ATRIAL ARRHYTHMIA BY FAR-FIELD SENSING

(71) Applicant: CAMERON HEALTH, INC., St. Paul, MN (US)

(72) Inventors: Gust H. Bardy, Carnation, WA (US); William J. Rissmann, Deephaven, MN (US); Alan H. Ostroff, Pleasanton, CA (US); Paul J. Erlinger, San Clemente, CA (US); Venugopal Allavatam, Maple Grove, MN (US)

(73) Assignee: CAMERON HEALTH, INC., St. Paul, MN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/350,574

(22) Filed: Nov. 14, 2016

(65) Prior Publication Data

US 2017/0056681 A1    Mar. 2, 2017

Related U.S. Application Data

(60) Continuation of application No. 14/838,152, filed on Aug. 27, 2015, now Pat. No. 9,522,283, which is a
(Continued)

(51) Int. Cl.
*A61N 1/00* (2006.01)
*A61N 1/39* (2006.01)
(Continued)

(52) U.S. Cl.
CPC ............ *A61N 1/3925* (2013.01); *A61B 5/046* (2013.01); *A61B 5/0452* (2013.01);
(Continued)

(58) Field of Classification Search
CPC .... A61N 1/3624; A61N 1/395; A61N 1/3956; A61B 5/0452; A61B 5/046; A61B 5/0464–5/0472
See application file for complete search history.

(56) References Cited

U.S. PATENT DOCUMENTS 3,258,732 A    6/1966    Martin
3,566,860 A    3/1971    Moe
(Continued)

FOREIGN PATENT DOCUMENTS

DE    29801801 UI    3/1998
DE    29801807 UI    6/1998
(Continued)

OTHER PUBLICATIONS

"U.S. Appl. No. 10/949,877, Response filed Mar. 18, 2009 to Restriction Requirement dated Sep. 18, 2008", 8 pgs.
(Continued)

*Primary Examiner* — Scott Getzow
(74) *Attorney, Agent, or Firm* — Seager, Tufte & Wickhem LLP

(57) ABSTRACT

In a subcutaneous implantable cardioverter/defibrillator, cardiac arrhythmias are detected to determine necessary therapeutic action. Cardiac signal information is sensed from far field electrodes implanted in a patient. The sensed cardiac signal information is then amplified and filtered. Parameters such as rate, QRS pulse width, cardiac QRS slew rate, amplitude and stability measures of these parameters from the filtered cardiac signal information are measured, processed and integrated to determine if the cardioverter/defibrillator needs to initiate therapeutic action.

18 Claims, 4 Drawing Sheets

Related U.S. Application Data continuation of application No. 14/245,119, filed on Apr. 4, 2014, now Pat. No. 9,138,589, which is a continuation of application No. 13/897,805, filed on May 20, 2013, now Pat. No. 8,750,989, which is a continuation of application No. 13/231,613, filed on Sep. 13, 2011, now Pat. No. 8,457,737, which is a division of application No. 12/122,432, filed on May 16, 2008, now Pat. No. 8,027,720, which is a continuation of application No. 10/863,599, filed on Jun. 8, 2004, now Pat. No. 7,379,772, which is a continuation of application No. 09/990,510, filed on Nov. 21, 2001, now Pat. No. 8,754,528.

(51) Int. Cl.
  *A61B 5/0452* (2006.01)
  *A61B 5/0456* (2006.01)
  *A61B 5/046* (2006.01)

(52) U.S. Cl.
  CPC ............ *A61B 5/0456* (2013.01); *A61N 1/395* (2013.01); *A61N 1/3931* (2013.01); *A61N 1/3956* (2013.01); *A61N 1/3987* (2013.01)

(56) References Cited

U.S. PATENT DOCUMENTS

| | | |
|---|---|---|
| 3,593,718 A | 7/1971 | Krasner et al. |
| 3,598,128 A | 8/1971 | Chardack |
| 3,653,387 A | 4/1972 | Ceier |
| 3,707,974 A | 1/1973 | Raddi |
| 3,710,374 A | 1/1973 | Kelly |
| 3,713,449 A | 1/1973 | Muller |
| 3,737,897 A | 6/1973 | Cuthbert et al. |
| 3,807,411 A | 4/1974 | Harris et al. |
| 3,822,707 A | 7/1974 | Adducci et al. |
| 3,827,046 A | 7/1974 | Watson |
| 3,828,766 A | 8/1974 | Krasnow |
| 3,841,312 A | 10/1974 | Corasanti |
| 3,842,842 A | 10/1974 | Kenny et al. |
| 3,866,616 A | 2/1975 | Purdy et al. |
| 3,908,668 A | 9/1975 | Bolduc |
| 3,911,925 A | 10/1975 | Tillery, Jr. |
| 3,941,135 A | 3/1976 | von Sturm et al. |
| 3,951,154 A | 4/1976 | Hartlaub |
| 3,986,496 A | 10/1976 | Brastad |
| 3,987,799 A | 10/1976 | Purdy et al. |
| 3,999,555 A | 12/1976 | Person |
| 4,010,758 A | 3/1977 | Rockland et al. |
| 4,010,759 A | 3/1977 | Boer |
| 4,013,081 A | 3/1977 | Kolenik |
| 4,030,509 A | 6/1977 | Heilman et al. |
| 4,057,067 A | 11/1977 | Lajos |
| 4,057,068 A | 11/1977 | Comben |
| 4,094,321 A | 6/1978 | Muto |
| 4,127,134 A | 11/1978 | Ushakoff |
| 4,141,752 A | 2/1979 | Shipko |
| 4,164,946 A | 8/1979 | Langer |
| 4,166,465 A | 9/1979 | Esty et al. |
| 4,184,493 A | 1/1980 | Langer et al. |
| 4,191,942 A | 3/1980 | Long |
| 4,210,149 A | 7/1980 | Heilman et al. |
| RE30,387 E | 8/1980 | Denniston, III et al. |
| 4,236,525 A | 12/1980 | Sluetz et al. |
| 4,248,237 A | 2/1981 | Kenny |
| 4,254,775 A | 3/1981 | Langer |
| 4,256,115 A | 3/1981 | Bilitch |
| 4,270,549 A | 6/1981 | Heilman |
| 4,290,430 A | 9/1981 | Bihn et al. |
| 4,291,707 A | 9/1981 | Heilman et al. |
| 4,300,567 A | 11/1981 | Kolenik et al. |
| 4,314,095 A | 2/1982 | Moore et al. |
| 4,335,756 A | 6/1982 | Sharp et al. |
| 4,349,030 A | 9/1982 | Belgard et al. |
| 4,351,345 A | 9/1982 | Carney |
| 4,354,509 A | 10/1982 | Strahwald |
| 4,375,817 A | 3/1983 | Engle et al. |
| 4,402,322 A | 9/1983 | Duggan |
| 4,406,286 A | 9/1983 | Stein |
| 4,412,541 A | 11/1983 | Schaldach et al. |
| 4,424,818 A | 1/1984 | Doring et al. |
| 4,450,527 A | 5/1984 | Sramek |
| 4,498,478 A | 2/1985 | Bourgeois |
| 4,543,956 A | 10/1985 | Herscovici |
| 4,548,209 A | 10/1985 | Wielders et al. |
| 4,553,554 A | 11/1985 | Lemole |
| 4,567,900 A | 2/1986 | Moore |
| 4,574,800 A | 3/1986 | Peers-Trevarton |
| 4,595,009 A | 6/1986 | Leinders |
| 4,602,637 A | 7/1986 | Elmqvist et al. |
| 4,603,705 A | 8/1986 | Speicher et al. |
| 4,628,937 A | 12/1986 | Hess et al. |
| 4,686,988 A | 8/1987 | Sholder |
| 4,693,253 A | 9/1987 | Adams |
| 4,702,253 A | 10/1987 | Nappholz et al. |
| 4,719,920 A | 1/1988 | Alt et al. |
| 4,727,877 A | 3/1988 | Kallok |
| 4,750,494 A | 6/1988 | King |
| 4,757,817 A | 7/1988 | Healy |
| 4,765,341 A | 8/1988 | Mower et al. |
| 4,768,512 A | 9/1988 | Imran |
| 4,821,724 A | 4/1989 | Whigham et al. |
| 4,825,871 A | 5/1989 | Cansell |
| 4,827,932 A | 5/1989 | Ideker et al. |
| 4,830,006 A | 5/1989 | Haluska et al. |
| 4,865,037 A | 9/1989 | Chin et al. |
| 4,865,566 A | 9/1989 | Rasmussen |
| 4,878,497 A | 11/1989 | Callaghan et al. |
| 4,901,079 A | 2/1990 | Nagashima et al. |
| 4,940,054 A | 7/1990 | Grevis et al. |
| 4,944,300 A | 7/1990 | Saksena |
| 4,969,463 A | 11/1990 | Dahl et al. |
| 5,003,990 A | 4/1991 | Osypka |
| 5,018,522 A | 5/1991 | Mehra |
| 5,020,544 A | 6/1991 | Dahl et al. |
| 5,036,854 A | 8/1991 | Schollmeyer et al. |
| 5,044,374 A | 9/1991 | Lindemans et al. |
| 5,050,600 A | 9/1991 | Parks et al. |
| 5,083,562 A | 1/1992 | De Coriolis et al. |
| 5,086,772 A * | 2/1992 | Larnard ............ A61N 1/3962 607/4 |
| 5,105,810 A | 4/1992 | Collins et al. |
| 5,105,826 A | 4/1992 | Smits et al. |
| 5,107,836 A | 4/1992 | Fenster |
| 5,109,842 A | 5/1992 | Adinolfi |
| 5,111,811 A | 5/1992 | Smits |
| 5,133,353 A | 7/1992 | Hauser |
| 5,144,946 A | 9/1992 | Weinberg et al. |
| 5,170,784 A | 12/1992 | Ramon et al. |
| 5,179,946 A | 1/1993 | Weiss |
| 5,191,901 A | 3/1993 | Dahl et al. |
| 5,193,535 A | 3/1993 | Bardy et al. |
| 5,215,081 A | 6/1993 | Ostroff |
| 5,235,977 A | 8/1993 | Hirschberg et al. |
| 5,243,977 A | 9/1993 | Tabucco et al. |
| 5,243,978 A | 9/1993 | Duffin, Jr. |
| 5,255,692 A | 10/1993 | Neubauer et al. |
| 5,261,400 A | 11/1993 | Bardy |
| 5,261,401 A | 11/1993 | Baker et al. |
| 5,265,623 A | 11/1993 | Kroll et al. |
| 5,269,810 A | 12/1993 | Hull et al. |
| 5,292,338 A | 3/1994 | Bardy |
| 5,292,810 A | 3/1994 | Manabe et al. |
| 5,300,110 A | 4/1994 | Latterell |
| 5,306,261 A | 4/1994 | Alliger et al. |
| 5,306,291 A | 4/1994 | Kroll et al. |
| 5,312,441 A | 5/1994 | Mader et al. |
| 5,313,953 A | 5/1994 | Yomtov et al. |
| 5,314,430 A | 5/1994 | Bardy |
| 5,318,591 A | 6/1994 | Causey, III et al. |
| 5,327,909 A | 7/1994 | Kiser et al. |
| 5,330,505 A | 7/1994 | Cohen |
| 5,330,523 A | 7/1994 | Campbell et al. |

(56) References Cited

U.S. PATENT DOCUMENTS

| | | |
|---|---|---|
| 5,331,966 A | 7/1994 | Bennett et al. |
| 5,342,400 A | 8/1994 | Hirschberg et al. |
| 5,342,407 A | 8/1994 | Dahl et al. |
| 5,344,430 A | 9/1994 | Berg et al. |
| 5,344,432 A | 9/1994 | Slettenmark et al. |
| 5,354,328 A | 10/1994 | Doan et al. |
| 5,358,514 A | 10/1994 | Schulman |
| 5,360,442 A | 11/1994 | Dahl et al. |
| 5,366,485 A | 11/1994 | Kroll et al. |
| 5,370,669 A | 12/1994 | Daglow et al. |
| 5,376,104 A | 12/1994 | Sakai et al. |
| 5,383,913 A | 1/1995 | Schiff |
| 5,385,575 A | 1/1995 | Adams |
| 5,388,578 A | 2/1995 | Yomtov et al. |
| 5,391,191 A | 2/1995 | Holmstrom |
| 5,391,200 A | 2/1995 | Kenknight et al. |
| 5,405,363 A | 4/1995 | Kroll et al. |
| 5,411,537 A | 5/1995 | Munshi et al. |
| 5,411,547 A | 5/1995 | Causey, III |
| 5,413,591 A | 5/1995 | Knoll |
| 5,423,326 A | 6/1995 | Wang et al. |
| 5,431,166 A | 7/1995 | Macur |
| 5,431,681 A | 7/1995 | Helland |
| 5,431,684 A | 7/1995 | Archer et al. |
| 5,431,692 A | 7/1995 | Hansen et al. |
| 5,439,485 A | 8/1995 | Mar et al. |
| 5,441,518 A | 8/1995 | Adams et al. |
| 5,447,519 A | 9/1995 | Peterson |
| 5,447,521 A | 9/1995 | Anderson et al. |
| 5,470,345 A | 11/1995 | Hassler et al. |
| 5,476,503 A | 12/1995 | Yang |
| 5,477,855 A | 12/1995 | Schindler et al. |
| 5,479,503 A | 12/1995 | Fujiwara |
| 5,489,293 A | 2/1996 | Pless et al. |
| 5,507,781 A | 4/1996 | Kroll et al. |
| 5,507,785 A | 4/1996 | Deno |
| 5,509,923 A | 4/1996 | Middleman et al. |
| 5,509,924 A | 4/1996 | Paspa et al. |
| 5,509,928 A | 4/1996 | Acken |
| 5,514,160 A | 5/1996 | Kroll et al. |
| 5,522,853 A | 6/1996 | Kroll |
| 5,531,764 A | 7/1996 | Adams et al. |
| 5,531,765 A | 7/1996 | Pless |
| 5,534,022 A | 7/1996 | Hoffmann et al. |
| 5,545,188 A | 8/1996 | Bradshaw et al. |
| 5,549,615 A | 8/1996 | Hocherl et al. |
| 5,573,003 A | 11/1996 | Mann et al. |
| 5,597,956 A | 1/1997 | Ito et al. |
| 5,601,607 A | 2/1997 | Adams |
| 5,601,608 A | 2/1997 | Mouchawar |
| 5,603,732 A | 2/1997 | Dahl et al. |
| 5,606,320 A | 2/1997 | Kleks |
| 5,607,455 A | 3/1997 | Armstrong |
| 5,618,287 A | 4/1997 | Fogarty et al. |
| 5,620,477 A | 4/1997 | Pless et al. |
| 5,641,326 A | 6/1997 | Adams |
| 5,643,323 A | 7/1997 | Kroll et al. |
| 5,643,328 A | 7/1997 | Cooke et al. |
| 5,645,572 A | 7/1997 | Kroll et al. |
| 5,645,586 A | 7/1997 | Meltzer |
| 5,658,317 A | 8/1997 | Haefner et al. |
| 5,658,319 A | 8/1997 | Kroll |
| 5,658,321 A | 8/1997 | Fayram et al. |
| 5,658,325 A | 8/1997 | Augustine |
| 5,662,696 A | 9/1997 | Kroll et al. |
| 5,674,260 A | 10/1997 | Weinberg |
| 5,690,648 A | 11/1997 | Fogarty et al. |
| 5,690,683 A | 11/1997 | Haefner et al. |
| 5,697,953 A | 12/1997 | Kroll et al. |
| 5,709,644 A | 1/1998 | Bush |
| 5,709,709 A | 1/1998 | Kroll |
| 5,713,926 A | 2/1998 | Hauser et al. |
| 5,718,242 A | 2/1998 | McClure et al. |
| 5,749,904 A | 5/1998 | Gliner et al. |
| 5,755,743 A | 5/1998 | Volz et al. |
| 5,766,226 A | 6/1998 | Pederson |
| 5,769,874 A | 6/1998 | Dahlberg |
| 5,772,690 A | 6/1998 | Kroll |
| 5,776,169 A | 7/1998 | Schroeppel |
| 5,782,891 A | 7/1998 | Hassler et al. |
| 5,797,968 A | 8/1998 | Lopin et al. |
| 5,800,464 A | 9/1998 | Kieval |
| 5,800,470 A | 9/1998 | Stein et al. |
| 5,814,090 A | 9/1998 | Latterell et al. |
| 5,827,326 A | 10/1998 | Kroll et al. |
| 5,836,976 A | 11/1998 | Min et al. |
| 5,849,031 A | 12/1998 | Martinez et al. |
| 5,871,506 A | 2/1999 | Mower |
| 5,871,508 A | 2/1999 | Thompson et al. |
| 5,873,897 A | 2/1999 | Armstrong et al. |
| 5,895,414 A | 4/1999 | Sanchez-Zambrano |
| 5,897,585 A | 4/1999 | Williams |
| 5,902,331 A | 5/1999 | Bonner et al. |
| 5,904,705 A | 5/1999 | Kroll et al. |
| 5,916,238 A | 6/1999 | Hauser et al. |
| 5,919,211 A | 7/1999 | Adams |
| 5,919,222 A | 7/1999 | Hjelle et al. |
| 5,925,069 A | 7/1999 | Graves et al. |
| 5,928,270 A | 7/1999 | Ramsey, III |
| 5,935,154 A | 8/1999 | Westlund |
| 5,941,904 A | 8/1999 | Johnston et al. |
| 5,944,669 A | 8/1999 | Kaib |
| 5,944,730 A | 8/1999 | Nobles et al. |
| 5,957,956 A | 9/1999 | Kroll et al. |
| 5,963,429 A | 10/1999 | Chen |
| 5,964,787 A | 10/1999 | Kerver et al. |
| 5,968,079 A | 10/1999 | Warman et al. |
| 5,978,703 A | 11/1999 | Kroll et al. |
| 5,978,705 A | 11/1999 | Kenknight et al. |
| 5,978,707 A | 11/1999 | Krig et al. |
| 5,987,352 A | 11/1999 | Klein et al. |
| 6,006,133 A | 12/1999 | Lessar et al. |
| 6,014,586 A | 1/2000 | Weinberg et al. |
| 6,026,325 A | 2/2000 | Weinberg et al. |
| 6,038,484 A | 3/2000 | Kuzma et al. |
| 6,056,722 A | 5/2000 | Jayaraman |
| 6,076,014 A | 6/2000 | Alt |
| 6,091,989 A | 7/2000 | Swerdlow et al. |
| 6,093,982 A | 7/2000 | Kroll |
| 6,095,987 A | 8/2000 | Shmulewitz et al. |
| 6,096,063 A | 8/2000 | Lopin et al. |
| 6,112,124 A | 8/2000 | Loeb et al. |
| H001905 H | 10/2000 | Hill |
| 6,128,531 A | 10/2000 | Campbell-smith |
| 6,144,866 A | 11/2000 | Miesel et al. |
| 6,148,230 A | 11/2000 | Kenknight |
| 6,169,921 B1 | 1/2001 | Kenknight et al. |
| 6,169,923 B1 | 1/2001 | Kroll |
| 6,176,879 B1 | 1/2001 | Reischl et al. |
| 6,185,450 B1 | 2/2001 | Seguine et al. |
| 6,187,028 B1 | 2/2001 | Munshi |
| 6,208,895 B1 | 3/2001 | Sullivan et al. |
| 6,241,751 B1 | 6/2001 | Morgan et al. |
| 6,249,707 B1 | 6/2001 | Kohnen et al. |
| 6,253,108 B1 | 6/2001 | Rosborough et al. |
| 6,256,541 B1 | 7/2001 | Heil et al. |
| 6,256,543 B1 | 7/2001 | Spence |
| 6,269,266 B1 | 7/2001 | Leysieffer |
| 6,272,379 B1 | 8/2001 | Fischell et al. |
| 6,272,385 B1 | 8/2001 | Bishay et al. |
| 6,278,894 B1 | 8/2001 | Salo et al. |
| 6,283,985 B1 | 9/2001 | Harguth et al. |
| 6,334,071 B1 | 12/2001 | Lu |
| 6,342,041 B1 | 1/2002 | Saint-Ramon et al. |
| 6,345,198 B1 | 2/2002 | Mouchawar et al. |
| 6,409,675 B1 | 6/2002 | Turcott |
| 6,411,844 B1 | 6/2002 | Kroll et al. |
| 6,438,407 B1 | 8/2002 | Ousdigian et al. |
| 6,445,956 B1 | 9/2002 | Laird et al. |
| 6,501,983 B1 | 12/2002 | Natarajan et al. |
| 6,508,771 B1 | 1/2003 | Padmanabhan et al. |
| 6,519,493 B1 | 2/2003 | Florio et al. |
| 6,522,915 B1 | 2/2003 | Ceballos et al. |
| 6,539,257 B1 | 3/2003 | Kenknight |

(56) References Cited

U.S. PATENT DOCUMENTS

| | | |
|---|---|---|
| 6,539,260 B1 | 3/2003 | Schloss |
| 6,647,292 B1 | 11/2003 | Bardy et al. |
| 6,658,296 B1 | 12/2003 | Wong et al. |
| 6,711,443 B2 | 3/2004 | Osypka |
| 6,721,528 B1 | 4/2004 | Schreieder et al. |
| 6,721,597 B1 | 4/2004 | Bardy et al. |
| 6,754,528 B2 | 6/2004 | Bardy et al. |
| 6,757,311 B2 | 6/2004 | Abe |
| 6,812,842 B2 | 11/2004 | Dimmer |
| 6,950,105 B2 | 9/2005 | Giemborek et al. |
| 6,954,669 B1 | 10/2005 | Fishler et al. |
| 6,980,856 B2 | 12/2005 | Sullivan et al. |
| 6,996,434 B2 | 2/2006 | Marcovecchio et al. |
| 7,020,523 B1 | 3/2006 | Lu et al. |
| 7,027,858 B2 | 4/2006 | Cao et al. |
| 7,031,774 B1 | 4/2006 | Doan et al. |
| 7,039,463 B2 | 5/2006 | Marcovecchio |
| 7,043,299 B2 | 5/2006 | Erlinger et al. |
| 7,065,410 B2 | 6/2006 | Bardy et al. |
| 7,069,075 B2 | 6/2006 | Olson |
| 7,076,295 B1 | 7/2006 | Kroll |
| 7,103,415 B2 | 9/2006 | Probst et al. |
| 7,379,772 B2 | 5/2008 | Bardy et al. |
| 7,570,997 B2 | 8/2009 | Lovett et al. |
| 7,865,233 B2 | 1/2011 | Haefner |
| 8,027,720 B2 | 9/2011 | Bardy et al. |
| 8,457,737 B2 | 6/2013 | Bardy et al. |
| 8,718,760 B2 | 5/2014 | Bardy et al. |
| 8,750,989 B2 | 6/2014 | Bardy et al. |
| 2001/0027330 A1 | 10/2001 | Sullivan et al. |
| 2002/0082658 A1 | 6/2002 | Heinrich et al. |
| 2002/0091414 A1* | 7/2002 | Bardy .................. A61N 1/375 607/4 |
| 2002/0103510 A1* | 8/2002 | Bardy .................. A61N 1/375 607/5 |
| 2002/0107544 A1* | 8/2002 | Ostroff ................. A61N 1/375 607/4 |
| 2002/0107546 A1* | 8/2002 | Ostroff ................. A61N 1/375 607/5 |
| 2002/0107547 A1* | 8/2002 | Erlinger .............. A61N 1/3956 607/5 |
| 2002/0107548 A1* | 8/2002 | Bardy .................. A61N 1/375 607/5 |
| 2002/0107549 A1* | 8/2002 | Bardy .................... A61N 1/05 607/5 |
| 2002/0107559 A1* | 8/2002 | Sanders ............... A61N 1/375 607/129 |
| 2002/0120296 A1 | 8/2002 | Mech et al. |
| 2002/0120299 A1* | 8/2002 | Ostroff ................. A61N 1/375 607/5 |
| 2002/0147475 A1 | 10/2002 | Scheiner et al. |
| 2003/0017372 A1 | 1/2003 | Probst et al. |
| 2003/0088278 A1* | 5/2003 | Bardy ................. A61N 1/3956 607/5 |
| 2003/0125785 A1 | 7/2003 | Kuzma et al. |
| 2003/0179123 A1 | 9/2003 | DeVilbiss |
| 2004/0093037 A1 | 5/2004 | Henry |
| 2004/0215239 A1 | 10/2004 | Favet et al. |
| 2004/0220641 A1 | 11/2004 | Wagner et al. |
| 2005/0021093 A1 | 1/2005 | Brown |
| 2005/0038476 A1 | 2/2005 | Brown |
| 2005/0055056 A1 | 3/2005 | Olson |
| 2005/0107838 A1 | 5/2005 | Lovett et al. |
| 2005/0119707 A1 | 6/2005 | Hauser et al. |
| 2005/0131464 A1 | 6/2005 | Heinrich et al. |
| 2005/0143776 A1 | 6/2005 | Brown |
| 2005/0195084 A1 | 9/2005 | Dimmer et al. |
| 2006/0015163 A1 | 1/2006 | Brown |
| 2006/0174898 A1 | 8/2006 | Brown |
| 2006/0217770 A1 | 9/2006 | Olson |
| 2007/0135847 A1 | 6/2007 | Kenknight |
| 2008/0140139 A1 | 6/2008 | Heinrich et al. |
| 2008/0269813 A1 | 10/2008 | Greenhut et al. |
| 2008/0319503 A1 | 12/2008 | Honeck et al. |
| 2013/0253356 A1 | 9/2013 | Bardy et al. |

FOREIGN PATENT DOCUMENTS

| | | |
|---|---|---|
| EP | 095727 A1 | 12/1983 |
| EP | 0134367 A1 | 3/1985 |
| EP | 0316616 A2 | 5/1989 |
| EP | 0347353 A1 | 12/1989 |
| EP | 0348708 A2 | 1/1990 |
| EP | 0316616 A3 | 6/1992 |
| EP | 0518599 A2 | 12/1992 |
| EP | 0536873 A1 | 4/1993 |
| EP | 0586858 A1 | 3/1994 |
| EP | 0641573 A2 | 3/1995 |
| EP | 677301 A1 | 10/1995 |
| EP | 0586858 B1 | 3/1997 |
| EP | 0641573 A3 | 6/1997 |
| EP | 0518599 B1 | 9/1997 |
| EP | 0536873 B1 | 9/1997 |
| EP | 0917887 A1 | 5/1999 |
| EP | 0923130 A1 | 6/1999 |
| EP | 1000634 A1 | 5/2000 |
| EP | 1517494 B1 | 6/2009 |
| EP | 1453573 B1 | 7/2013 |
| JP | 4327450 B2 | 9/2009 |
| WO | 9220402 A1 | 11/1992 |
| WO | 9319809 A1 | 10/1993 |
| WO | 9825349 A1 | 6/1998 |
| WO | 9903534 A1 | 1/1999 |
| WO | 9937362 A1 | 7/1999 |
| WO | 0041766 A1 | 7/2000 |
| WO | 0050120 A1 | 8/2000 |
| WO | 0143649 A1 | 6/2001 |
| WO | 0156166 A2 | 8/2001 |
| WO | 0222205 A1 | 3/2002 |
| WO | 02068046 A1 | 9/2002 |
| WO | 03018121 A2 | 3/2003 |

OTHER PUBLICATIONS

"U.S. Appl. No. 10/949,877, Response filed Oct. 19, 2009 to Non Final Office Action dated Apr. 20, 2009", 33 pgs.

"U.S. Appl. No. 10/949,877, Restriction Requirement dated Sep. 18, 2008", 11 pgs.

"U.S. Appl. No. 10/949,877, Supplemental Preliminary Amendment filed Apr. 13, 2005", 29 pgs.

"U.S. Appl. No. 10/968,889, Examiner Interview Summary dated Mar. 22, 2010", 3 pgs.

"U.S. Appl. No. 10/968,889 Examiner Interview Summary dated Apr. 14, 2009", 2 pgs.

"U.S. Appl. No. 10/968,889 Examiner Interview Summary dated Apr. 16, 2009", 2 pgs.

"U.S. Appl. No. 10/968,889 Examiner Interview Summary dated May 28, 2008", 2 pgs.

"U.S. Appl. No. 10/968,889 Final Office Action dated Jul. 13, 2010", 18 pgs.

"U.S. Appl. No. 10/968,889, Non Final Office Action dated Apr. 17, 2009", 13 pgs.

"U.S. Appl. No. 10/968,889, Non Final Office Action dated Oct. 17, 2008", 14 pgs.

"U.S. Appl. No. 10/968,889, Response Filed Apr. 28, 2010 to Restriction Requirement dated Dec. 30, 2009", 5 pgs.

"U.S. Appl. No. 10/968,889 Response Filed Jun. 5, 2008 to Restriction Requirement dated Dec. 6, 2007", 3 pgs.

"U.S. Appl. No. 10/968,889 Response Filed Oct. 19, 2009 to Non Final Office Action dated Apr. 17, 2009", 58 pgs.

"U.S. Appl. No. 10/968,889 Restriction Requirement dated Dec. 6, 2007", 6 pgs.

"U.S. Appl. No. 10/968,889 Restriction Requirement dated Dec. 30, 2009", 11 pgs.

"U.S. Appl. No. 10/968,889, Supplemental Preliminary Amendment filed Apr. 11, 2005", 33 pgs.

(56) References Cited

OTHER PUBLICATIONS

"U.S. Appl. No. 11/447,711, Final Office Action dated Apr. 7, 2009", 11 pgs.
"U.S. Appl. No. 11/447,711, Final Office Action dated Jun. 19, 2009", 7 pgs.
"U.S Appl. No. 11/447,711, Non Final Office Action dated Nov. 7, 2008", 10 pgs.
"U.S. Appl. No, 11/447,711, Notice of Allowance dated Sep. 23, 2009", 5 pgs.
"U.S. Appl. No. 11/447,711, Response Filed Feb. 6, 2009 to Non Final Office Action dated Nov. 7, 2008", 10 pgs.
"U.S. Appl. No. 11/447,711, Response filed Jun. 8, 2009 to Final Office Action dated Apr. 7, 2009", 9 pgs.
"U.S. Appl. No. 11/447,711, Response filed Aug. 3, 2009 to Final Office Action dated Jun. 19, 2009", 3 pgs.
"U.S. Appl. No. 11/529,671, Non Final Office Action dated May 1, 2009", 7 pp.
"U.S. Appl. No. 11/529,671, Non Final Office Action dated Nov. 14, 2008", 8 pgs.
"U.S. Appl. No. 11/529,671, Notice of Allowance dated Dec. 31, 2009", 5 pgs.
"U.S Appl. No. 11/529,671, Response Filed Feb. 6, 2009 to Non Final Office Action dated Nov. 14, 2008", 9 pgs.
"U.S. Appl. No. 11/529,671, Response Filed Aug. 3, 2009 to Non Final Office Action dated May 1, 2009", 3 pgs.
"U.S. Appl. No. 60/252,811, filed Nov. 22, 2000", 19 pgs.
"European Application Serial No. 01973151.2, Communication under Rule 71(3) EPC dated Mar. 3, 2014", 9 pgs.
"European Application Serial No. 01973151.2, Office Action dated Jan. 20, 2011", 5 pgs.
"European Application Serial No. 01973151.2, Office Action dated Aug. 28, 2006", 4 pgs.
"European Application Serial No. 01973151.2, Response Filed May 19, 2011 to Office Action dated Jan. 20, 2011", 16 pgs.
"European Application Serial No. 01973151.2, Response Filed Dec. 20, 2006 to Office Action dated Aug. 28, 2006", 22 pgs.
"European Application Serial No. 01973151.2, Summons to Attend Oral Proceedings dated Oct. 11, 2013", 6 pgs.
"International Application Serial No. PCT/IB2002/003447, International Preliminary Examination Report dated Sep. 2, 2003", 5 pgs.
"International Application Serial No. PCT/IB2002/003447, International Search Report dated Feb. 20, 2003", 6 pgs.
"International Application Serial No. PCT/IB2002/003447, Written Opinion dated May 12, 2003", 5 pgs.
"International Application Serial No. PCT/IB2002/003452, International Preliminary Examination Report dated Sep. 2, 2003", 5 pgs.
"International Application Serial No. PCT/IB2002/003452, International Search Report dated Feb. 14, 2003", 4 pgs.
"International Application Serial No. PCT/IB2002/003452, Written Opinion dated May 12, 2003", 5 pgs.
"International Application Serial No. PCT/IB2002/003453, International Preliminary Examination Report dated Sep. 2, 2003", 5 pgs.
"International Application Serial No. PCT/IB2002/003453, International Search Report dated Feb. 14, 2003", 4 pgs.
"International Application Serial No. PCT/IB2002/003453, Written Opinion dated May 12, 2003", 5 pgs.
"International Application Serial No. PCT/IB2002/003467, International Preliminary Examination Report dated Sep. 2, 2003", 5 pgs.
"International Application Serial No. PCT/IB2002/003467, International Search Report dated Feb. 14, 2003", 4 pgs.
"International Application Serial No. PCT/IB2002/003467, Written Opinion dated May 12, 2003", 5 pgs.
'International Application Serial No. PCT/IB2002/003469, International Preliminary Examination Report dated Sep. 2, 2003', 5 pgs.
"International Application Serial No. PCT/IB2002/003469, Written Opinion dated May 12, 2003", 5 pgs.

Chrysostomakis et al., "Sensing Issues Related to the Clinical Use of Implantable Loop Recorders", Europace; vol. 5(2), pp. 143-148, 2003.
Higgins et al., "The First Year Experience with the Dual Chamber ICD", Pace, vol. 23, pp. 18-25, Jan. 2000.
Hoffman et al., Experience with pectoral versus abdominal implantation of a small defibrillator, European Heart Journal, vol. 19., pp. 1085-1098, Jul. 1998.
Krahn et al., "Maturation of the Sensed Electogram Amplitude Over Time in a New Subcutaneous Implantable Loop Recorder", PACE, vol. 20(6), pp. 1686-1690, Jun. 1997.
Olson et al., "Onset & Stability for Ventricular Tachyarrhythmia Detection in an Implantable Pacer-Cardioverter-Defibrillator", IEEE Computers in Cardiology vol. 0276-6574, pp. 167-170, 1987.
Park et al., "Use of an Implantable Cardioverter Defibrillator.in an Eight-Month-Old Infant with Ventricular Fibrillation Arising from Myocardial Fibroma", Pace, vol. 22, pp. 138-139, Jan. 1999.
Tietze et al., "Halbleiter-Schaltungstechnik", Springer Verlag, Berlin, Germany, pp. 784-786, 1991.
Valenzuela et al., "Outcomes of Rapid Defibrillation by Security Officers After Cardiac Arrest In Casinos", The New England Journal in Medicine, vol. 343(17), pp. 1206-1209, Oct. 2000.
Walters et al., "Analog to Digital Conversion Techniques in Implantable Devices", Annual International Conference of the IEEE Engineering in Medicine and Biology Society, vol. 13(4), pp. 1674-1676, 1991.
Zellerhoff et al., "How Can We Identity the Best Implantation Site for and ECG Event Recorder?", Pace; vol. 23(10), pp. 1545-1549, Oct. 2000.
"U.S. Appl. No. 10/863,599, Non Final Office Action dated Apr. 2, 2007", 6 pgs.
"U.S. Appl. No. 10/863,599, Non Final Office Action dated Aug. 14, 2007", 4 pgs.
"U.S. Appl. No. 10/863,599, Response filed Jun. 12, 2007 to Non Final Office Action dated Apr. 2, 2007", 8 pgs.
"U.S. Appl. No. 10/863,599, Response filed Nov. 7, 2007 to Non Final Office Action dated Aug. 14, 2007", 8 pgs.
"U.S. Appl. No. 12/122,432, Non Final Office Action dated Dec. 29, 2010", 7 pgs.
"U.S. Appl. No. 12/122,432, Non Final Office Action dated Mar. 29, 2010", 6 pgs.
"U.S. Appl. No. 13/231,613, Non Final Office Action dated Oct. 22, 2012", 6 pgs.
"U.S. Appl. No. 13/231,613, Response filed Dec. 20, 2012, to Non Final Office Action dated Oct. 22, 2012", 7 pgs.
"U.S. Appl. No. 13/887,652, Response filed Nov. 14, 2013, to Non Final Office Action dated Aug. 14, 2013", 9 pgs.
"U.S. Appl. No. 13/897,805, Non Final Office Action dated Oct. 9, 2013", 7 pgs.
"U.S. Appl. No. 13/897,805, Notice of Allowance dated Feb. 5, 2014", 6 pgs.
"U.S. Appl. No. 13/897,805, Response filed Dec. 19, 2013 to Non Final Office Action dated Oct. 9, 2013", 9 pgs.
Throne et al., "A Comparison of Four New Time-Domain Techniques for Discriminating Monomorphic Ventricular Tachycardia from Sinus Rhythm Using Ventricular Waveform Morphology", IEEE Transactions on Biomedical Engineering, vol. 38(6), pp. 561-570, Jun. 1991.
M948140A001C, (May 10, 2012), 22 pgs.
"U.S. Appl. No. 10/949,877, Response filed Feb. 1, 2011 to Final Office Action dated Jan. 4, 2010", 35 pages.
"International Application Serial No. PCT/IB2002/003469, International Search Report dated Feb. 14, 2003", 4 pgs.
Bardy et. al., "Multicenter Experience with a Pectoral Unipolar Implantable Cardioverter-Defibrillator", JACC, vol. 28 (2), 400-410, Aug 1996.
"International Application Serial No. PCT/IB2002/003481, International Preliminary Examination Report dated Sep. 2, 2003", 5 pgs.
"International Application Serial No. PCT/IB2002/003481, International Search Report dated Feb. 20, 2003", 4 pgs.

(56) References Cited

OTHER PUBLICATIONS

"International Application Serial No. PCT/IB2002/003484, International Preliminary Examination Report dated Sep. 2, 2003", 5 pgs.
"International Application Serial No. PCT/IB2002/003484, International Search Report dated Feb. 14, 2003", 5 pgs.
"International Application Serial No. PCT/IB2002/003484, Written Opinion dated May 12, 2003", 5 pgs.
"International Application Serial No. PCT/IB2002/003488, International Preliminary Examination Report dated Sep. 2, 2003", 5 pgs.
"International Application Serial No. PCT/IB2002/003488, International Search Report dated Feb. 14, 2003", 4 pgs.
"International Application Serial No. PCT/IB2002/003488, Written Opinion dated May 12, 2003", 5 pgs.
"International Application Serial No. PCT/IB2002/003501, International Preliminary Examination Report dated Sep. 2, 2003", 5 pgs.
"International Application Serial No. PCT/IB2002/003501, International Search Report dated Feb. 20, 2003", 4 pgs.
"International Application Serial No. PCT/IB2002/003501, Written Opinion dated May 12, 2003", 5 pgs.
"International Application Serial No. PCT/IB2002/003502, International Preliminary Examination Report dated Sep. 2, 2003", 5 pgs.
"International Application Serial No. PCT/IB2002/003502, International Search Report dated Feb. 20, 2003", 4 pgs.
"International Application Serial No. PCT/IB2002/003502, Written Opinion dated May 12, 2003", 5 pgs.
"International Application Serial No. PCT/IB2002/003503, International Preliminary Examination Report dated Sep. 2, 2003", 5 pgs.
"International Application Serial No. PCT/IB2002/003503, International Search Report dated Feb. 18, 2003", 4 pgs.
"International Application Serial No. PCT/IB2002/003503, Written Opinion dated May 12, 2003", 5 pgs.
"International Application Serial No. PCT/IB2002/003522, International Preliminary Examination Report dated Sep. 2, 2003", 5 pgs.
"International Application Serial No. PCT/IB2002/003522, International Search Report dated Feb. 14, 2003", 4 pgs.
"International Application Serial No. PCT/IB2002/003522, Written Opinion dated May 12, 2003", mailed 6 pgs.
"International Application Serial No. PCT/IB2002/003525, International Preliminary Examination Report dated Sep. 2, 2003", 5 pgs.
"International Application Serial No. PCT/IB2002/003525 International Search Report dated Feb. 20, 2003", 5 pgs.
"International Application Serial No. PCT/IB2002/003525, Written Opinion dated May 12, 2003", 5 pgs.
International Application Serial No. PCT/IB2002/004454 International Search Report dated Mar. 28, 2003, 3 pgs.
"International Application Serial No. PCT/IB2002/004475 International Search Report dated Apr. 25, 2003", 4 pgs.
"International Application Serial No. PCT/IB2002/004476 International Search Report dated May 8, 2003", 2 pgs.
"International Application Serial No. PCT/IB2002/004490 International Search Report dated Apr. 16 2003", 3 pgs.
"International Application Serial No. PCT/IB2002/004497 International Search Report dated Apr. 23, 2003", 3 pgs.
"International Application Serial No. PCT/IB2002/004498 International Search Report dated Apr. 16, 2003", 8 pgs.
"International Application Serial No. PCT/IB2002/004507 International Search Report dated Apr. 16, 2003", 4 pgs.
"International Application Serial No. PCT/IB2002/004513 International Search Report dated Mar. 6, 2003", 5 pgs.
"International Application Serial No. PCT/IB2002/004514, International Search Report dated May 8, 2003", 4 pgs.
"International Application Serial No. PCT/IB2002/004515 International Search Report dated Apr. 23, 2003", 1 pg.
"International Application Serial No. PCT/IB2002/004516 International Search Report dated Apr. 16, 2003", 4 pgs.
"International Application Serial No. PCT/IB2003/004498 International Search Report dated Apr. 16, 2003", 2 pgs.
"International Application Serial No. PCT/IB2003/004516 International Search Report dated Apr. 16, 2003", 3 pgs.
"International Application Serial No. PCT/IB2003/004543 International Search Report dated Apr. 16, 2003", 4 pgs.
"International Application Serial No. PCT/IB2003/004546 International Search Report dated Apr. 16, 2003", 4 pgs.
"International Application Serial No. PCT/US2001/029106 International Preliminary Examination Report dated Dec. 18, 2002", 6 pgs.
"International Application Serial No. PCT/US2001/029106 International Search Report dated Mar. 21, 2002", 4 pgs.
"International Application Serial No. PCT/US2001/029106 Written Opinion dated Sep. 3, 2002".
"International Application Serial No. PCT/US2001/029168 International Preliminary Examination Report dated Nov. 20, 2002", 7 pgs.
"International Application Serial No. PCT/US2001/029168, International Search Report dated Mar. 26, 2002", 5 pgs.
"International Application Serial No. PCT/US2001/029168 Written Opinion dated Sep. 10, 2002", 7 pgs.
"International Application Serial No. PCT/US2003/010666 International Search Report dated Oct. 1, 2003", 1 pg.
"Japanese Application Serial No. 2006-533540, Office Action dated Mar. 2, 2010", (w/ English Translation), 6 pgs.
"Japanese Application Serial No. 2006-533540, Response Filed Aug. 2, 2010 to Office Action dated Mar. 2, 2010", (w) English Translation), 3 pgs.
"Medtronic 6996SQ Subcutaneous, unipolar lead with defibrillation coil electrode", Technical Manual, Medtronic, Inc., M948140A001C, (May 10, 2012), 22 pgs.
Boecker et al, "Treatment with implantable defibrillators in childhood", Herzschrittmachertherapie and Elektrophysiologie, vol. 10 (4), pp. 248-251, Dec. 1999.
Chrysostomakis et al., "Implantable Loop Recorder Undersensing Mimicking Complete Heart Block", Europace; vol. 4(2), pp. 211-213, 2002.

\* cited by examiner

APPARATUS AND METHOD FOR IDENTIFYING ATRIAL ARRHYTHMIA BY FAR-FIELD SENSING

RELATED APPLICATIONS

This application is a continuation of U.S. patent application Ser. No. 14/838,152, filed Aug. 27, 2015, which is a continuation of U.S. patent application Ser. No. 14/245,119, filed Apr. 4, 2014, now U.S. Pat. No. 9,138,589, which is a continuation of U.S. patent application Ser. No. 13/897,805, filed May 20, 2013, now U.S. Pat. No. 8,750,989, which is a continuation of U.S. patent application Ser. No. 13/231,613, filed Sep. 13, 2011, now U.S. Pat. No. 8,457,737, which is a divisional of U.S. patent application Ser. No. 12/122,432, filed May 16, 2008, now U.S. Pat. No. 8,027,720 and titled APPARATUS AND METHOD OF ARRHYTHMIA DETECTION IN A SUBCUTANEOUS IMPLANTABLE CARDIOVERTER/DEFIBRILLATOR; which is a continuation of U.S. patent application Ser. No. 10/863,599, filed Jun. 8, 2004, now U.S. Pat. No. 7,379,772 and titled APPARATUS AND METHOD OF ARRHYTHMIA DETECTION IN A SUBCUTANEOUS IMPLANTABLE CARDIOVERTER/DEFIBRILLATOR; which is a continuation of U.S. patent application Ser. No. 09/990,510, filed Nov. 21, 2001, now U.S. Pat. No. 6,754,528 and titled APPARATUS AND METHOD OF ARRHYTHMIA DETECTION IN A SUBCUTANEOUS IMPLANTABLE CARDIOVERTER/DEFIBRILLATOR; the entire disclosures of which are hereby incorporated by reference.

FIELD

The subject invention relates generally to implantable cardioverter/defibrillators and, more particularly, to detection of cardiac arrhythmias with subcutaneous implantable cardioverter/defibrillators.

BACKGROUND

Defibrillation/cardioversion is a technique employed to counter arrhythmic heart conditions including some tachycardias or fast heart rhythms originating in the atria and/or ventricles. Typically, electrodes are employed to stimulate the heart with electrical impulses or shocks of a magnitude substantially greater than pulses used in cardiac pacing. A variety of shock waveforms are used for both defibrillation and pacing, including truncated exponentially decaying monophasic and biphasic waveform pulses as well as pulses where the waveform maintains a relatively constant current over the duration of delivery to the myocardium.

Defibrillation/cardioversion systems include body implantable electrodes that are connected to a hermetically sealed container housing the electronics, battery supply and capacitors. The entire system is referred to as an implantable cardioverter/defibrillator (ICD). The electrodes used in ICDs can be in the form of patches applied directly to epicardium, or, more commonly, the electrodes are located on the distal regions of small cylindrical insulated catheters that typically enter the subclavian venous system, pass through the superior vena cava, and into one or more endocardial areas of the heart. Such electrode systems are called intravascular or transvenous electrodes. U.S. Pat. Nos. 4,603,705; 4,693,253; 4,944,300; and 5,105,810, the disclosures of which are all incorporated herein by reference, disclose intravascular or transvenous electrodes, employed either alone, in combination with other intravascular or transvenous electrodes, or in combination with an epicardial patch or subcutaneous electrodes. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat. No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active canister electrode, and therefore, it has no practical use. It has, in fact, never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs that are small enough to be implanted in the infraclavicular pectoral region, a site allowing access to the subclavian venous system. In addition, advances in circuit design have enabled the housing of the ICD to form a subcutaneous electrode. Some examples of ICDs in which the housing of the ICD serves as an optional additional electrode are described in U.S. Pat. Nos. 5,133,353; 5,261,400; 5,620,477; and 5,658,321 the disclosures of which are incorporated herein by reference.

ICDs are now an established therapy for the management of life-threatening cardiac rhythm disorders, primarily ventricular fibrillation (VF) and also ventricular tachycardia (VT). ICDs are very effective at treating VF and VT, but traditional ICD implantation still requires significant surgery and surgical skill, especially regarding lead insertion into the venous system and lead positioning in the heart.

As ICD therapy becomes more prophylactic in nature and used in progressively less ill individuals, including children, the requirement of ICD therapy to use intravenous catheters and transvenous leads is a major impediment to very long-term management as most individuals will develop complications related to lead system malfunction, fracture or infection sometime in the 5- to 10-year time frame, often earlier. In addition, chronic transvenous lead systems, their removal and reimplantation, can damage major cardiovascular venous systems and the tricuspid valve, as well as result in life-threatening perforations of the great vessels and heart. Consequently, use of transvenous lead systems, despite their many known advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of a related therapy, the automatic external defibrillator (AED) AEDs employ the use of cutaneous patch electrodes, rather than implantable lead systems, to effect defibrillation under the direction of a bystander user who treats the patient suffering from VF with a portable device containing the necessary electronics and power supply that allows defibrillation. AEDs can be nearly as effective as an ICD for defibrillation if applied to the victim of ventricular fibrillation promptly, i.e., within 2 to 3 minutes of the onset of the ventricular fibrillation. AEDs, unlike ICDs, only make shock/no-shock decisions, as they are relieved of the burden of needing to deliver complicated tiered therapeutic responses that the ICD encumbers as a consequence of detecting and treating a multitude of rhythm problems with a multitude of therapies. AEDs either shock for a life-threatening event or they do not shock. ICDs, on the other hand, are designed for a variety of interventions and use a different technological approach for arrhythmia detection, redetection, assessment of effectiveness and therapy.

AED therapy has great appeal as a tool for diminishing the risk of death in public venues such as in airplanes. However, an AED must be used by another individual, not the person suffering from the potential fatal rhythm. It is more of a public health tool than a patient-specific tool like an ICD. Because >75% of cardiac arrests occur in the home, and over half occur in the bedroom, patients at risk of cardiac arrest are often alone or asleep and cannot be helped in time with an AED. Moreover, its success depends to a reasonable degree on an acceptable level of skill and calm by the bystander user.

What is needed, therefore, for life-threatening arrhythmias, especially for children and for prophylactic long-term use for adults at risk of cardiac arrest, is a novel combination of the two forms of therapy which would provide prompt and near-certain defibrillation, like an ICD, but without the long-term adverse sequelae of a transvenous lead system while simultaneously harboring most of the simpler diagnostic and therapeutic technological approaches of an AED. What is also needed is a cardioverter/defibrillator that is of simple design and can be comfortably implanted in a patient for many years.

Further, an ICD is needed that can detect various types of cardiac arrhythmias to provide a patient with adequate therapy according to the type of cardiac arrhythmia experienced by the patient. Although ICDs have multiple secondary functions, they primarily have two key functions: detection and therapy of life-threatening cardiac arrhythmias. ICDs constantly monitor a patient's cardiac activity and analyze the cardiac activity to determine the appropriate therapy that should be delivered to the patient. The type of therapies available to be delivered to the patient include pacing, which can be single or dual chamber, therapy to correct slow heart rates or bradycardia called anti-bradycardia pacing, therapy to correct slow and moderately fast ventricular tachycardia (VT) and sometimes atrial tachyarrhythmias, called anti-tachycardia pacing (ATP), and therapy to correct ventricular fibrillation (VF) or high energy shocks. Thus, given the various types of therapies available, it is very important to classify the type of cardiac arrhythmias appropriately.

Detection schemes of cardiac arrhythmias are characterized using two indexes of performance: sensitivity and specificity. Sensitivity generally refers to the ability of the detection scheme or algorithm to accurately detect an abnormal heart rhythm for which the physician desires the device to treat. Specificity generally refers to the ability of the detection scheme or algorithm to not treat rhythms that the physician determines the device should not treat, such as sinus tachycardia. Sensitivity values for VT/VF are typically between 90% to 98%. There is constantly a tradeoff between the ability to detect an abnormal rhythm and the desire to prevent treatment of a normal rhythm. The higher the sensitivity, the more likely the detection algorithm will result in an inappropriate therapy of a normal rhythm and, thus, lower specificity. The higher the specificity, the less likely the device will be able to detect rhythms that should be treated and, thus, the lower the sensitivity. Despite a desire to limit false positive interventions, specificity values are typically only between 70% to 90% in order to not miss therapy of a life-threatening disorder. In practice, there is a constant tension between sensitivity and specificity.

Factors influencing detection algorithm performance include hardware performance, lead electrode placement, electrode design, electrode shape, inter-electrode spacing and the analytical capabilities and design of the detection scheme itself. Because ICDs are battery powered and, therefore, an unlimited supply of power is not available to perform complex and power intensive analytical functions, the energy required to perform the analytical functions is also a factor influencing detection scheme performance.

Another factor that influences the sensitivity and specificity performance of a detection algorithm is the clinical balance between false negatives and false positives for each arrhythmia that the detection algorithm is required to detect. The more arrhythmias required to detect, the more overlap and complexity in the algorithm. For example, one might require a very high sensitivity for fast VT/VF, given its lethality, and therefore accept a lower specificity compared to the relatively benign arrhythmia of atrial fibrillation (AF).

A false negative therapeutic decision results from a detection scheme that calls a bona fide treatable event "normal". But, depending upon the arrhythmia, some false negatives are more tolerable than others. On the other end of the spectrum is a false positive therapeutic decision that results from a detection algorithm that calls a "normal" event an "abnormal" event, thus inappropriately indicating that therapy should be delivered. False positives for therapy of VT are more clinically acceptable than false positives for rhythms like AF where the former is immediately life-threatening and the later is seldom so.

A false negative can result in a missed arrhythmia and can lead to death, and a false positive may result in an inappropriate shock that will be uncomfortable, but not life threatening. Therefore, it is understandable that detection algorithms are skewed to result in false positives and reduce the occurrence of false negatives to zero for rhythms like fast VT but are more common for rhythms like AF where lower sensitivity is more clinically acceptable. Performance of typical detection schemes in current devices result in approximately 15% to 45% false positives for life-threatening disorders like VF and fast VT.

Typically, ICDs primarily use a rate-based classification scheme. That is, the intervals between successive heart beats are measured and, depending on their values, they are classified as slow, normal, or fast. Slow heart beats are treated with pacing (i.e., anti-bradycardia pacing), when the rate reaches a critically low level, according to a physician's direction via the programming of the device. Programmable parameters for slow heart rates include primarily rate and hysteresis. Normal heart rates are left alone, where normal is usually defined in the range of 40-100 bpm. Fast heart beats are often further classified into three zones with various therapies ascribed to each zone. For example, the lowest zone may have a series of anti-tachycardia pacing (ATP) therapies maneuvers programmed for rhythms like monomorphic VT that may fall in this lowest tachycardia rate zone. The next higher zone may integrate a limited number of ATP attempts with a moderate energy shock therapy of approximately between 5-10 Joules for that zone. Finally, the highest zone may have a scheme programmed to deliver the highest output shock energy for rhythms falling in this zone having VF or VT with the fastest and therefore most life-threatening rates.

Additional rate-based qualifiers have been used to improve the specificity of detection schemes. Examples of such qualifiers include parameters like sudden onset to eliminate false positive detection of sinus tachycardia and heart rate interval stability to eliminate false positive detection of rapid AF for VT. Sudden onset refers to tachyarrhythmias that are a result of a precipitous increase in heart rate as opposed to sinus tachycardia where the higher rates tend to come on gradually. The term stability in detection algorithms usually, but not always, refers to the coupling interval between heart beats as a way to distinguish the characteristically irregular interval-to-interval time sequence of AF from more regular cardiac rhythms like sinus tachycardia or monomorphic ventricular tachycardia where the interval-to-interval time sequence is more regular and rarely varies by more than 30 ms unlike AF where variation by 40 ms or more is the rule. Although typically faster in rate, VF does, like AF, exhibit interval-to-interval instability. It can be distinguished from AF in a detection algorithm mostly by its typically much faster rate but also by overlaying other measures in addition to rate and interval-to-interval stability that result from an examination of the electrocardiographic QRS features.

The term stability, when used in detection algorithms, can have another meaning and refer to electrocardiogram (ECG) QRS signal stability, i.e., the ability of the QRS to have identical or at least very similar signal characteristics on a beat-to-beat basis. In one example of stability, one can examine QRS duration or width, QRS amplitude, QRS slew rate (rate of change of the voltage signal), QRS signal template matching, and/or QRS signal frequency content as an indicator of beat-to-beat stability. VF, for example, under this example of stability would be highly unstable as the QRS is constantly changing in all of the ways indicated above in this paragraph. Confirming the presence of VF, regardless of rate, would aid dramatically in applying a shock/no-shock decision-making process.

Recent developments in QRS morphology measurements involve a scheme in which certain areas within a cardiac QRS complex are measured and compared against a normal set as defined by the physician at the time of implant or as defined automatically by the device during preset follow-up measurement intervals.

There are other issues that enter into the ability of ICDs to detect abnormal heart rhythms depending on the cardiac information that is actually presented to the device's sensing electrodes (which may represent only part of the complete set of cardiac information at any point in time), the ICD energy available to analyze the information, the time required or allowed to make the analysis, and the ability or lack thereof for the device to modify itself over time with respect to changes in the patient's underlying cardiac disease process or even such shorter duration events as changes in body positioning.

With respect to limitations in cardiac information available to the device's sensing electrodes, current devices use a first electrode at the tip deep inside the right ventricle as one half of an electrode sensing pair. The second electrode of the pair can be a shocking coil also in the right ventricle and in close proximity to the first electrode, a second cylindrical electrode approximately 0.5 to 2 cm away from the first tip electrode, or the metallic housing of the device itself. Because the first electrode is in close proximity to cardiac tissue, it is more sensitive to electric fields present in the tissue closest to it and less sensitive to the entire electric field generated by all of the cardiac tissue. This contrast to a subcutaneous ICD sensing pair that has the advantage of a true far-field cardiac signal.

With respect to the energy limitations of current devices, the ability to process and analyze cardiac signals depends on the energy available to the devices. Current devices are limited on the amount of energy available for analyzing signals because the devices must reserve a significant portion of the energy for pacing and shocking over the course of several years. For example, one measure of a device's performance is its ability to filter out unwanted signals, this is called common mode rejection ratio (CMRR). The higher the CMRR of a device, the better able it is to reject signals common to both electrodes. Current devices have a CMRR of about 50 db. Energy is required to achieve higher CMRR values. Another aspect of the analysis requiring energy is the use of a microprocessor with appropriate software inside the device to analyze cardiac information.

Continuous running of a microprocessor in an implantable device would result in a rapid battery drain with unacceptably short battery longevity. As a result, current devices reserve a portion of hardware dedicated to crude analysis of the underlying rhythm on a continuous basis and only activate the microprocessor when further analysis is needed. Once activated, the microprocessor, along with its software programming, further analyze the cardiac information, decide on a course of action and, when finished, go back to inactive mode.

For a subcutaneous only ICD, these issues of arrhythmia detection sensitivity and specificity, false positives and false negatives, battery depletion, and algorithm design require significantly different considerations and unique hardware considerations and algorithm design compared to typical ICDs with 1-2 sensing leads in immediate contact with the myocardium.

What is then needed is an implantable cardioverter/defibrillator that has different sensing capabilities to ensure that an ICD using only subcutaneous shocking and sensing electrodes performs at acceptable levels as well as has the ability to adapt itself to changes over time.

SUMMARY

According to one aspect of the invention, an apparatus and method are provided for detecting cardiac arrhythmias with a subcutaneous implantable cardioverter/defibrillator. The method includes the steps of sensing cardiac signal information from far field electrodes implanted in a patient, amplifying the sensed cardiac signal information, filtering the amplified cardiac signal information, measuring parameters such as rate, amplitude, QRS pulse width, cardiac slew rate, QRS signal frequency content, QRS morphology, and stability measures of these parameters, and processing and integrating the parameters of the cardiac signal information to determine if the cardioverter/defibrillator needs to initiate therapeutic action.

BRIEF DESCRIPTION OF THE DRAWINGS

For a better understanding of the invention, reference is now made to the drawings where like numerals represent similar objects throughout the figures where.

DETAILED DESCRIPTION

Figure 1:
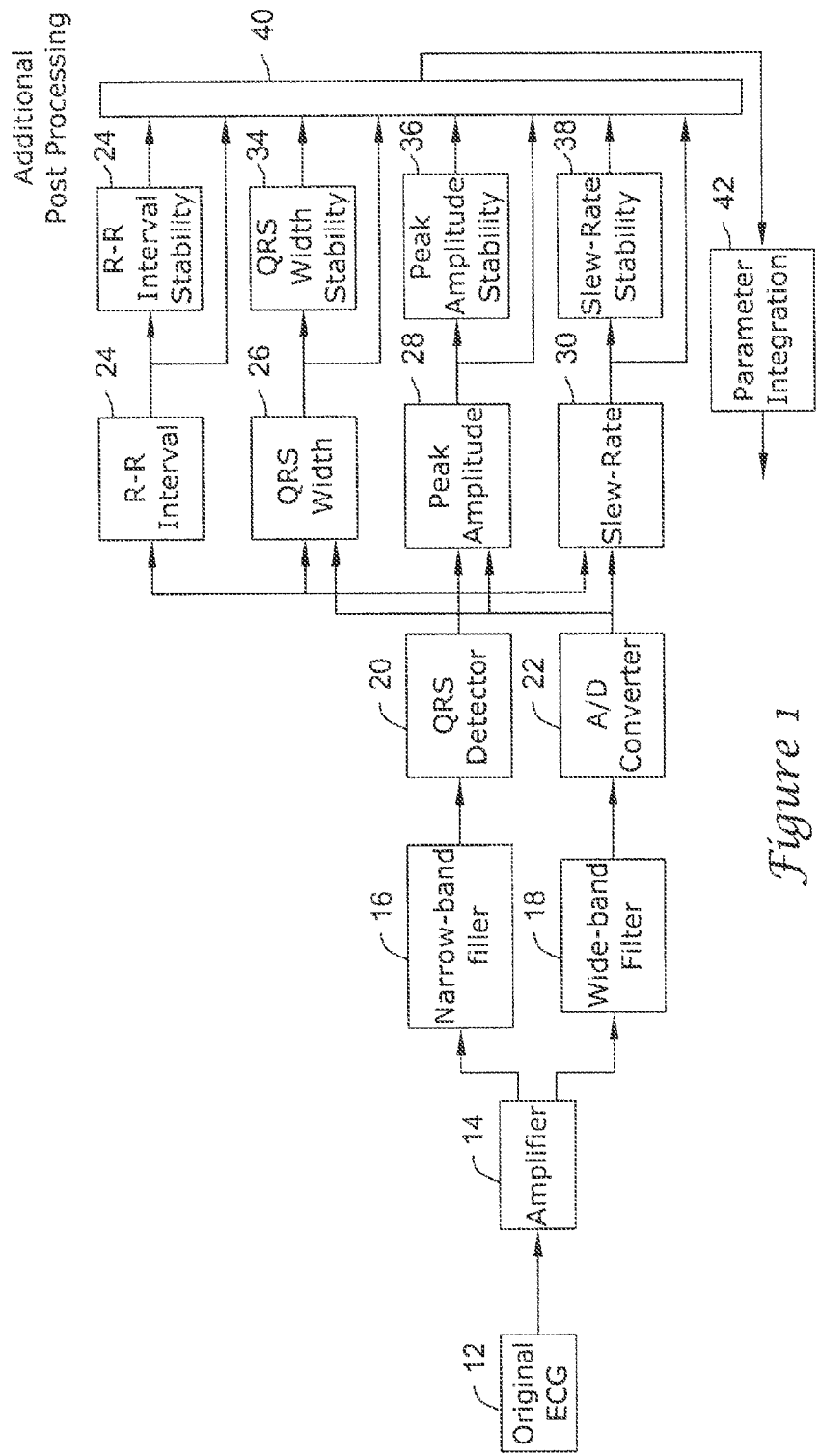
FIG. 1 is a block diagram of a cardiac arrhythmia detection scheme according to an embodiment of the present invention.

A flow diagram of an algorithm for detecting various types of cardiac arrhythmias is shown in FIG. 1 and is discussed below. The detection algorithm of the present invention has the ability to detect and treat ventricular rhythm disorders and withhold treatment for supraventricular arrhythmias such as AF. In certain embodiments, the detection algorithm of the present invention can be employed by a Subcutaneous Implantable Cardioverter-Defibrillator (S-ICD) or a Unitary Subcutaneous Implantable Cardioverter-Defibrillator (US-ICD), such as those described in US patent applications titled SUBCUTANEOUS ONLY IMPLANTABLE CARDIOVERTER-DEFIBRILLATOR AND OPTICAL PACER, having Ser. No. 09/663,607, now U.S. Pat. No. 6,721,597; and UNITARY SUBCUTANEOUS ONLY IMPLANTABLE CARDIOVERTER-DEFIBRILLATOR AND OPTIONAL PACER, having Ser. No. 09/663,606, now U.S. Pat. No. 6,647,292; of which both applications were filed Sep. 18, 2000, and the disclosures of both are hereby incorporated by reference. Although the algorithm is intended for the detection and therapy of life-threatening rhythm disorders like fast VT and VF, it may also be adapted for use in the treatment of AF (or other rhythm disorders) by accepting, rather than rejecting, for therapy the diagnosis of AF.

One feature of S-ICD and US-ICD devices that facilitates cardiac rhythm monitoring is the size and location of the lead. Far field cardiac signals are more easily detected by use of larger electrodes. The S-ICD and US-ICD devices typically use electrode size much larger than that used in standard ICD electrode systems for sensing VT/VF and thus are more appropriate for far field ECG sensing. In addition, the location in the $3^{rd}$ to $12^{th}$ rib space (such as between the $4^{th}$ to $6^{th}$ rib space in one example), provides a sufficient signal for detection of the cardiac rhythm with use of a subcutaneous-only ICD location. Examples of such S-ICD devices and electrodes that provide proper shapes, sizes and locations for the devices and electrodes are described in US patent applications titled SUBCUTANEOUS IMPLANTABLE CARDIOVERTER-DEFIBRILLATOR EMPLOYING A TELESCOPING LEAD, U.S. Ser. No. 10/011,941, now U.S. Pat. No. 7,043,299; and SUBCUTANEOUS ELECTRODE WITH IMPROVED CONTACT SHAPE FOR TRANSTHORACIC CONDUCTION, U.S. Ser. No. 10/013,980, now U.S. Pat. No. 7,065,410; of which both applications were filed Nov. 5, 2001, and the disclosures of both are hereby incorporated by reference.

In addition, S-ICD and US-ICD devices typically provide an electrode that is inward facing toward the heart to facilitate improved arrhythmia detection and rhythm monitoring. This design of the electrode compensates for not being directly in contact with the heart, like the sensing electrodes of the common transvenous ICD. The compensating features of this type of lead electrode for the S-ICD allow better rhythm detection by facing the myocardium and simultaneously avoiding or minimizing exposure to surface artifacts and noise that may be easily detected by subcutaneous sensing electrodes.

In addition, the S-ICD and the US-ICD devices have two or more electrodes that provide a far-field view of cardiac electrical activity that includes the ability to record the P-wave of the electrocardiogram as well as the QRS. In one embodiment of the present invention, the detection algorithm can detect the onset of AF by referencing to the P-wave recorded during normal sinus rhythm and monitoring for its change in rate, morphology, amplitude and frequency content as well as its timing and polarity relationship to the QRS. For example, a well-defined P-wave that abruptly disappears and is replaced by a low-amplitude, variable morphology signal would be a strong indication of the absence of sinus rhythm and the onset of AF. In an alternative embodiment of the detection algorithm, the ventricular detection rate could be monitored for stability of the R-R coupling interval. In the examination of the R-R interval sequence, AF can be recognized by providing irregularly spaced R-R intervals due to variable conduction of atrial beats to the ventricles through the atrioventricular node. An R-R interval plot during AF appears "cloudlike" in appearance when many R-R intervals are plotted over time and compared to sinus rhythm or other supraventricular arrhythmias. Moreover, a distinguishing feature of AF when compared to ventricular fibrillation is that the QRS morphology is similar on a beat-by-beat basis during AF despite the irregularity in the R-R coupling interval. In yet another embodiment, AF may be detected by seeking to compare the timing and amplitude relationship of the detected P-wave of the electrocardiogram to the detected QRS (R-wave) of the electrocardiogram. Normal sinus rhythm has a fixed relationship that can be placed into a template-matching algorithm that can be used as a reference point should the relationship change.

In other aspects of the AF detection process, one may include alternative electrodes that may be brought to bear in the S-ICD or US-ICD systems either by placing them in the detection algorithm circuitry through a programming maneuver or by manually adding such additional electrode systems to the S-ICD or US-ICD at the time of implant or at the time of follow-up evaluation. One may also use electrodes for the detection of AF that may or may not also be used for the detection of ventricular arrhythmias, given the different anatomic locations of the atria and ventricles with respect to the S-ICD or US-ICD housing and surgical implant sites.

Once AF is detected, therapy can be withheld since AF is relatively benign or the arrhythmia can be treated by delivery of a synchronized shock using energy levels up to the maximum output of the device therapy for terminating AF or for terminating other supraventricular arrhythmias. Synchronization can be conducted by detecting the onset of the QRS signal and delivering the atrial cardioversion shock during the synchronized time period. The S-ICD or US-ICD electrode system can be used to treat both atrial and ventricular arrhythmias not only with shock therapy but also with pacing therapy. In a further embodiment of the treatment of AF or other atrial arrhythmias, one may be able to use different electrode systems than what is used to treat ventricular arrhythmias. Another embodiment would be to allow for different types of therapies (amplitude, waveform, capacitance, etc.) for atrial arrhythmias compared to ventricular arrhythmias.

An algorithm for detecting various types of cardiac arrhythmias with an S-ICD or a US-ICD will be described below with respect to FIG. 1. It should be noted that although the following description refers to an S-ICD that employs the detection algorithm, the description also applies to a US-ICD. As described above, the S-ICD may be positioned between the third rib and the twelfth rib of a patient and uses a lead system that does not directly contact the patient's heart or reside in the intrathoracic blood vessels of the patient.

It is also known that while S-ICD and US-ICD devices are able to pace, the devices are not intended for long-term pacing. Typically, the S-ICD provides short-term pacing in the order of a few hours as an emergency therapy so that the patient can consult with a physician or other care-giver. As a result, some of the energy that would be used for pacing is available for better processing and sophisticated analysis of the sensed cardiac signals. Accordingly, the S-ICD has energy available to achieve CMRR values of approximately 70 db to 100 db, in one example.

As noted above, S-ICDs use signals gathered from far field electrodes as opposed to electrodes that are in contact with the heart of a patient. As a result, a more sophisticated set of features can be used to make a device with higher specificity performance characteristics. A variety of detection schemes are possible with both the information available by the electrode placement as well as with the processing power available.

In addition to the use of the sense circuitry for detection of atrial and ventricular information, sense circuitry can check for the presence or the absence of respiration. The respiration rate and/or minute volume can be detected by monitoring the impedance across the thorax using subthreshold currents delivered across the active can and the high voltage subcutaneous lead electrode (or the 2 canister electrodes in one US-ICD embodiment) and monitoring the frequency in undulation in the waveform that results from the undulations of transthoracic impedance during the respiratory cycle. If there is no undulation, then the patent is not respiring and this lack of respiration can be used to confirm the QRS findings of cardiac arrest. The impedance measurement using the S-ICD and US-ICD electrodes can also be used to extract stroke volume, ejection fraction or cardiac output measures providing a hemodynamic sensor input that can be combined with rate, QRS signal frequency content, QRS morphology, and stability measures of these parameters to further refine the shock/no-shock decision-making process.

The activity level of the patient can also be detected using miniature 1-D, 2-D or 3-D accelerometer. Piezo-electric crystals can also be used as a sensor to determine the activity level of the patient. Activity level of the patient can be another input parameter used by the detection algorithm to further refine the shock/no-shock decision-making process.

Even the patient's position can be detected by using a miniature mercury switch that is actuated when the patient is horizontal. The patient's position can be used as another input parameter to the detection algorithm to further refine the shock/no-shock decision-making process.

Referring now to FIG. 1, a block diagram of a cardiac arrhythmia detection scheme according to an embodiment of the present invention is illustrated. The scheme uses elements comprising an electrocardiogram input 12, an amplifier 14, a narrow-band filter 16, a wide-band filter 18, a QRS detector 20, an analog-to-digital (A/D) converter 22, an R-R interval detector 24, a QRS width detector 26, a peak amplitude detector 28, a slew rate detector 30, an R-R interval stability detector 32, a QRS width stability detector 34, a peak amplitude stability detector 36, a slew-rate stability detector 38, additional post processor 40, and a parameter integrator 42.

Electrocardiogram (ECG) 12 comprises cardiac signal information sensed by the far field electrodes placed subcutaneously. In an embodiment, the signal information is sent to amplifier 14, which has a CMRR value of at least approximately 80 db. The signal information is then sent from amplifier 14 to narrow-band filter 16 and wide-band filter 18. In an example, narrow-band filter 16 has corners set at approximately 10 Hz and 30 Hz, and wide-band filter 18 has corners set at approximately 1 Hz and 50 Hz.

In an embodiment, from the narrow-band filter 16, the filtered signal information is presented to QRS detector 20 for purposes of identifying the timing of the QRS complex. From the wide-band filter 18, the filtered signal information is presented to A/D converter 22 for converting the signal information to a digital format.

From QRS detector 20, the signal information is presented to R-R interval detector 24, QRS width detector 26, peak amplitude detector 28 and/or slew rate detector 30. R-R interval detector 24 measures the time interval between each successive QRS complex. The signal information from R-R interval rate detector 24 can be further presented to R-R interval stability detector 32, which analyzes the variability between each successive QRS complex. QRS width detector 26 measures the time interval of the sampled QRS complex. The signal information from QRS width detector 26 can be further presented to QRS width stability detector 34, which analyzed the variability between the width of each successive QRS complex. Peak amplitude detector 28 measures the maximum amplitude of the sampled QRS complex. The signal information from peak amplitude detector 28 can be further presented to peak amplitude stability detector 36, which analyzes the variability between the peak amplitudes of each successive QRS complex. Slew rate detector 30 measures the slew rate of the sampled QRS complex. The signal information from slew rate detector 30 can be further presented to slew rate stability detector 38, which analyzes the variability between the slew rates of each successive QRS complex.

In an embodiment, after processing by R-R interval detector 24, R-R interval stability detector 32, QRS width detector 26, QRS width stability detector 34, peak amplitude detector 28, peak amplitude stability detector 36, slew rate detector 30 and/or the slew rate stability detector 38, the signal information can be presented to additional post processing 40 for further processing such as first derivative processing, second derivative processing, etc.

In an embodiment, from ND converter 22, the digitized cardiac signal information is further analyzed with respect to parameters including QRS complex width by QRS width detector 26, QRS peak amplitude by peak amplitude detector 28, and/or rising edge slew rate of the QRS complex by slew rate detector 30. From the QRS width detector 26, the peak amplitude detector 28, and the slew rate detector 30, the signal information can be further processed by additional post processors 40. Examples of additional processing may include adaptive filtering to avoid the slow-term effects that drugs or other substrate changes may have on the parameters, X out of Y filtering to avoid decisions based on single events, moving average filters, etc. In addition, first derivative processing, second derivative processing, etc., may also be accomplished.

In one embodiment of the detection algorithm, rate is measured on a continuous basis. Other parameters may have registers associated for fine tuning by a programmer and/or determined periodically or continually on a beat-by-beat basis during normal sinus rhythm (NSR) and used to enhance the detection algorithms effectiveness by compensating for the relatively slow-changing effects many of the input parameters may have due to body positional changes, substrate changes and drug effects.

For example, short-term or long-term NSR averages of QRS width and R-wave amplitude would help compute the variability of these parameters with greater insensitivity to cardiac substrate changes.

It is also envisaged that many if not all of these parameters will be stored on a beat-by-beat basis in a circular buffer, allowing more sophisticated algorithms to scan back in time and take into account the past behavior of the system.

In addition, to conserve power consumption, a predetermined threshold will be used to enable the advanced analysis when multiple input variables are evaluated. Several parameters such as rate, cardiac QRS pulse width, cardiac QRS slew rate, and the various measures of signal stability are, in one embodiment, measured on a continuous basis. In another embodiment, the non-rate measures may be turned on only when the rate exceeds a predetermined limit. The range of this predetermined limit could be 50-240 bpm. In one embodiment, the limit for activation of the non-rate detection measures would be 140 bpm. In another embodiment, the predetermined threshold that allows advanced analysis may be a measure other than rate, for example, QRS width or some other measure. In any case, each of these parameters has associated registers for fine tuning or modifying the parameters on either a periodic basis or a more dynamic basis such as that associated with body positional changes.

Figure 2:
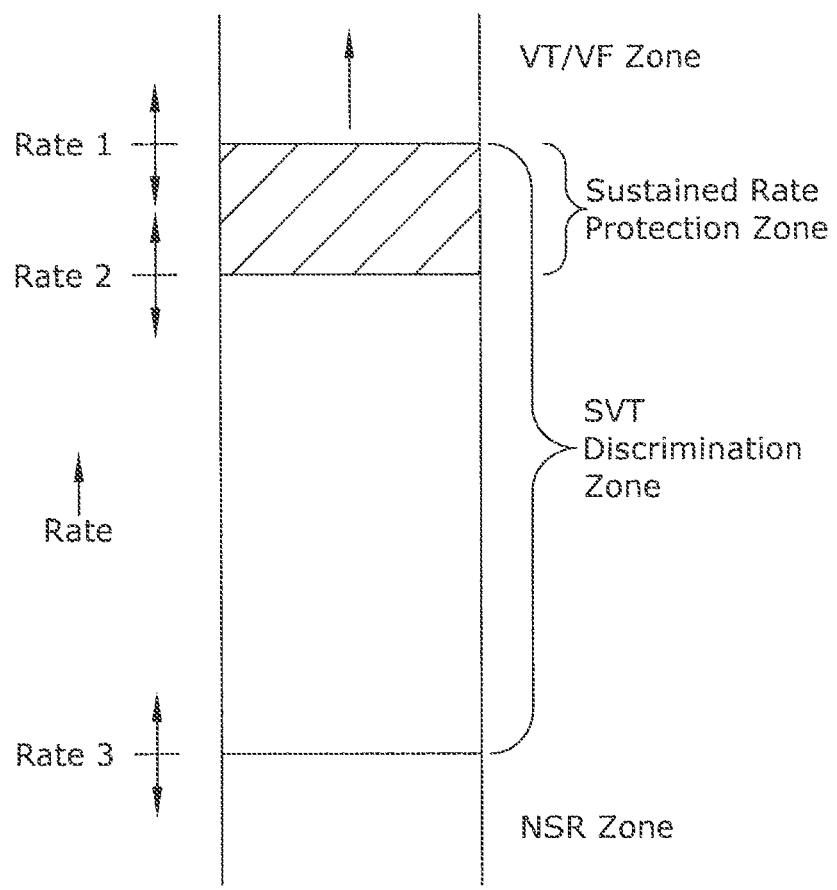
FIG. 2 is a diagram showing various heart zones for a cardiac arrhythmia detection scheme according to an embodiment of the present invention.
Figure 3:
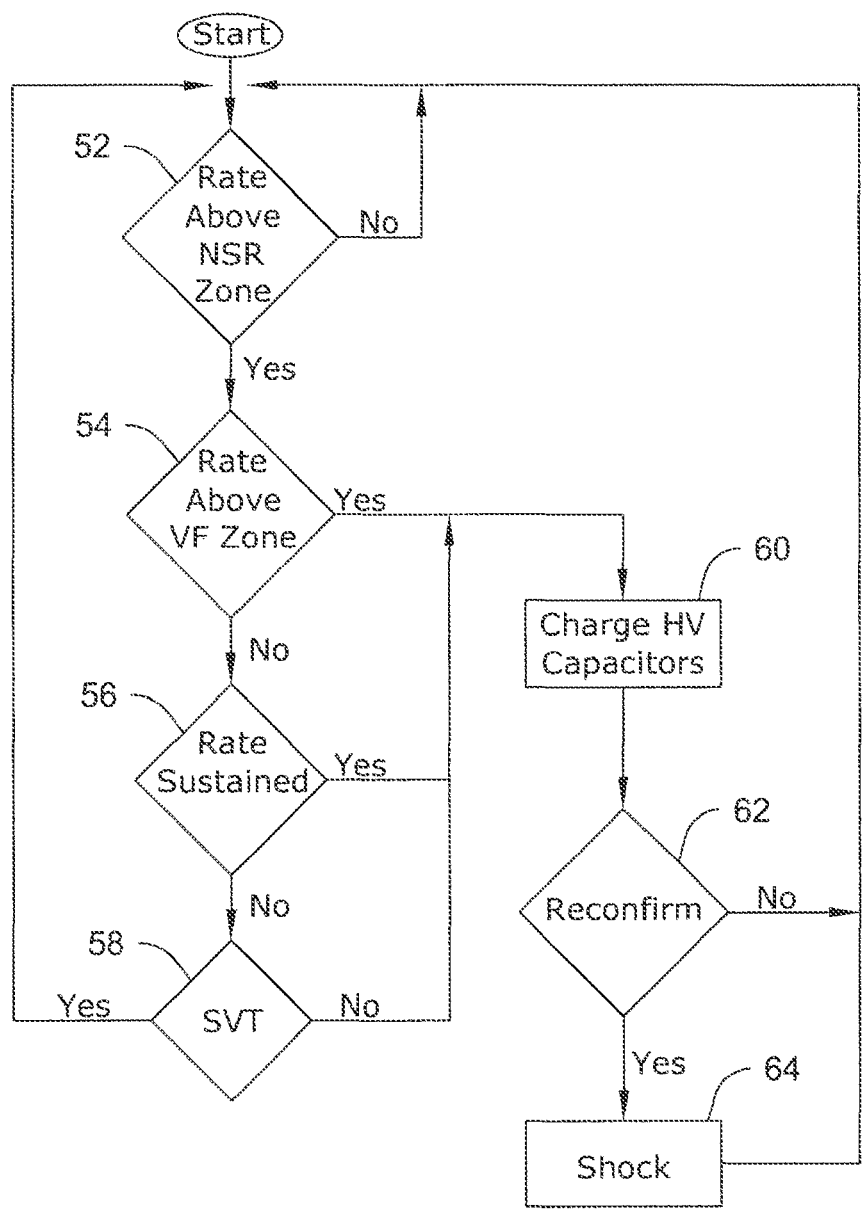
FIG. 3 is a flow diagram illustrating the interrelation of the detection scheme of FIG. 1 in an S-ICD according to an embodiment of the present invention.

FIG. 2 is a diagram showing various heart rate zones for a cardiac arrhythmia detection scheme according to an embodiment of the present invention. FIG. 3 is a flow diagram illustrating the interrelation of the detection scheme of FIG. 1 and the heart rate zones of FIG. 2 according to an embodiment of the present invention.

In one embodiment of the detection algorithm, rate is used as a first criterion in the detection algorithm. As shown in FIG. 2 and FIG. 3, four rate zones are defined, two of which can overlap each other. The first zone, defined as rates faster than Rate 1, define the fast VT and VF zone. Rates greater than Rate 1 will result in charging of the capacitors and immediate shock therapy. Rates between Rate 1 and Rate 2 are defined as a sustained VT/VF zone. Rates in this zone will only be treated if they persist for a pre-determined period, (for example, 20 seconds), even if the output of the parameter integration block 42 might indicate treatment should be withheld. The sustained rate zone can be disabled by effectively setting Rate 1 and Rate 2 equal. Rates between Rate 1 and Rate 3 define an SVT discrimination zone. Rates within the SVT discrimination zone enable further processing by the parameter integration block 42 shown in FIG. 1. The desired output of the parameter integration block 42 is a decision to apply shock treatment or withhold shock treatment due to non-shockable rhythms such as SVTs like AF. Finally, rates below Rate 3 are defined as the NSR zone. In an embodiment, these rates are not treated.

The parameter integration block 42 combines n-parameters to distinguish shockable rhythms from non-shockable rhythms. Numerous methods are well known in the art to process such n-parameters and to determine a desired sensitivity and specificity based on patient testing data. Some of these methods include statistical classifiers, fuzzy logic, artificial neural networks and rule-based systems. In operation, each of these methods constructs an integration block which can distinguish shockable and non-shockable rhythms from n parameters, or n dimensions. In one example, a statistical classifier can describe the decision boundary using only rate and QRS width stability criteria. These metrics or features are used to calculate scalar numbers or vectors that summarize the characteristics of the signals.

Figure 4:
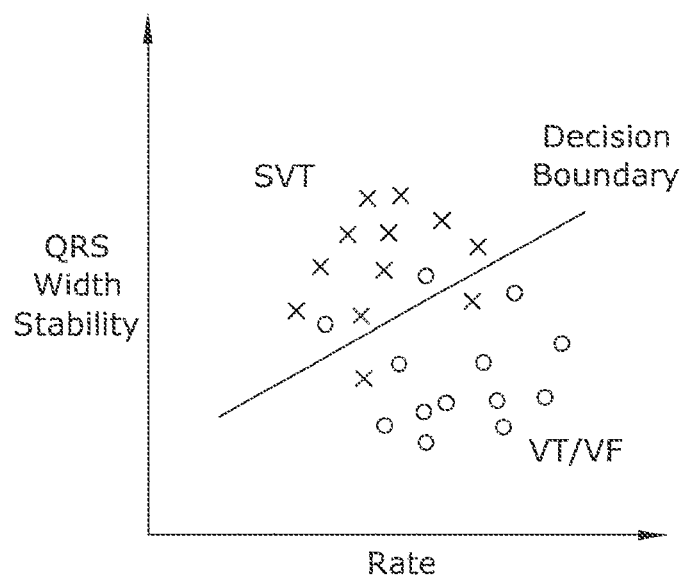
FIG. 4 is a diagram showing a shock/no-shock boundary for a cardiac arrhythmia detection scheme according to a two-dimensional embodiment of the present invention.

FIG. 4 is a diagram showing a shock/no-shock boundary for a cardiac arrhythmia detection scheme according to a two-dimensional embodiment of the present invention. More specifically, FIG. 4 shows two different classes of data from a graph relating QRS width stability to rate. One class of data identifies an SVT condition that should not be shocked. The other class identifies a VT/VF condition that should be shocked. As shown in FIG. 4, the two classes of data are separated by a decision boundary line. The decision boundary line can be drawn empirically, or determined analytically by computing the distance each feature vector lies with respect to the mean, weighted by the standard deviations of the class mean. These distances are known as the Mahanalobis distances. The decision boundary line can then be determined as the line equidistant from the means or centroids of the two classes in an attempt to separate the two classes of rhythms with the least misclassification error. In three dimensions, different classes can represent multiple clusters. Again, either a plane or surface plot can be determined empirically or analytically by computing Mahanalobis distances of the different classes using set of patient testing data. The decision to shock or not-shock is then determined by observing on which side of the boundary the feature vector lays.

In another embodiment, the decision to shock/no-shock can be performed with as few as one parameter. For example, a single scalar value can be set using QRS width. Beats with a QRS width wider than a threshold are classified as ventricular tachycardia. The threshold maximum may be fixed or may be adjusted based on NRS computed measures or other calculations to account for long-term cardiac substrate changes.

In another embodiment, a single parameter, such as rate, can be monitored such that once it reaches a threshold, the detection algorithm can then analyze other parameters to determine the shock/no-shock decision, thus conserving battery power.

In another embodiment, the decision to shock/no-shock can be performed with three parameters. For example, in three dimensions, one axis represents QRS stability, another axis represents QRS slew-rate and the third axis represents rate. The decision boundary can then be represented as a surface, which can be a simple plane or a more complex three-dimensional surface. The decision boundary surface can be computed analytically or empirically to determine the shock/no-shock decision. Such a surface could also be updated and changed according to a continuous or semi-continuous or periodic measurement of reference values for that patient.

While a two-dimensional embodiment of the detection algorithm is shown, other embodiments are possible such as an n-dimensional embodiment that employs n different input parameters.

Artificial neural networks can also be used to determine the shock/no-shock decision boundary by emulating the observed properties of biological nervous systems and drawing on the analogies of adaptive biological learning. The principal feature of artificial neural networks is a structure of highly interconnected processing elements that are analogous to neurons and are tied together with weighted connections that are analogous to synapses. Learning involves the changes that occur to the synaptic connections between neurons.

Neural networks are well suited to process n-dimensional input parameters and can be trained to produce a shock/no-shock decision often with imprecise or noisy data. Many different neural structures are possible. For example, one structure comprises a multilayer perceptron that is trained with a backpropagation of error algorithm, although numerous other structures and training algorithms could also be effective.

Numerous characteristics and advantages of the invention covered by this document have been set forth in the foregoing description. It will be understood, however, that this disclosure is, in many aspects, only illustrative. Changes may be made in details, particularly in matters of shape, size and arrangement of parts without exceeding the scope of the invention. The invention's scope is defined, of course, in the language in which the appended claims are expressed.

The invention claimed is:

1. An implantable medical device (IMD) configured for monitoring a patient's cardiac rhythm to determine whether an arrhythmia is occurring, the IMD comprising:
   a housing containing a battery and operational circuitry for the IMD, the operational circuitry comprising an ECG input, an amplifier, one or more filter circuits, and a detector configured to detect QRS events; and
   at least first and second electrodes on the housing and electrically coupled to the operational circuitry, the electrodes configured for sensing a cardiac signal of the patient;
   wherein the operational circuitry is configured to detect one or more QRS signals for the patient during a normal sinus rhythm;
   wherein the operational circuitry is further configured to detect atrial fibrillation (AF) by determining whether detected signals show an absence of P-waves between consecutive QRS signals by differentiating between a well-defined P-wave and a low-amplitude signal; and
   wherein the operational circuitry is configured to establish one or more parameters for P-waves associated with QRS signals including a polarity relationship of the P-wave to the QRS.

2. The IMD of claim 1 wherein the operational circuitry is configured to establish one or more parameters for P-waves associated with QRS signals including a rate of the P-wave.

3. The IMD of claim 1 wherein the operational circuitry is configured to establish one or more parameters for P-waves associated with QRS signals including a morphology of the P-wave.

4. The IMD of claim 1 wherein the operational circuitry is configured to establish one or more parameters for P-waves associated with QRS signals including an amplitude of the P-wave.

5. The IMD of claim 1 wherein the operational circuitry is configured to establish one or more parameters for P-waves associated with QRS signals including a frequency content of the P-wave.

6. The IMD of claim 1 wherein the operational circuitry is configured to establish one or more parameters for P-waves associated with QRS signals including a timing relative to the QRS.

7. The IMD of claim 1 wherein the operational circuitry is further configured to detect AF by monitoring for stability of the coupling interval between R-waves in the QRS signal and finding irregularly spaced R-waves.

8. The IMD of claim 1 wherein the operational circuitry is further configured, in the event that AF is not identified, to determine whether a cardiac rate of the patient exceeds a threshold and, if so, to deliver defibrillation therapy to the patient.

9. The IMD of claim 1 wherein the operational circuitry is further configured, in the event that AF is identified, to deliver cardioversion therapy to the patient to terminate the detected AF, further wherein the operational circuitry is configured to deliver the cardioversion therapy by detecting the onset of the QRS signal and delivering the cardioversion shock during a synchronized time period.

10. An implantable medical device (IMD) configured for monitoring a patient's cardiac rhythm to determine whether an arrhythmia is occurring, the IMD comprising:
    a housing containing a battery and operational circuitry for the IMD, the operational circuitry comprising an ECG input, an amplifier, one or more filter circuits, and a detector configured to detect QRS events; and
    at least a first electrode on the housing and electrically coupled to the operational circuitry, the first electrode configured for sensing a cardiac signal of the patient;
    at least a second electrode disposed on an implantable lead configured for coupling to the housing to electrically couple the second electrode to the operational circuitry, the second electrode configured for sensing a cardiac signal of the patient;
    wherein the operational circuitry is configured to detect one or more QRS signals for the patient during a normal sinus rhythm;
    wherein the operational circuitry is further configured to detect atrial fibrillation (AF) by determining whether detected signals show an absence of P-waves between consecutive QRS signals by differentiating between a well-defined P-wave and a low-amplitude signal; and
    wherein the operational circuitry is configured to establish one or more parameters for P-waves associated with QRS signals including a polarity relationship of the P-wave to the QRS.

11. The IMD of claim 10 wherein the operational circuitry is configured to establish one or more parameters for P-waves associated with QRS signals including a rate of the P-wave.

12. The IMD of claim 10 wherein the operational circuitry is configured to establish one or more parameters for P-waves associated with QRS signals including a morphology of the P-wave.

13. The IMD of claim 10 wherein the operational circuitry is configured to establish one or more parameters for P-waves associated with QRS signals including an amplitude of the P-wave.

14. The IMD of claim 10 wherein the operational circuitry is configured to establish one or more parameters for P-waves associated with QRS signals including a frequency content of the P-wave.

15. The IMD of claim 10 wherein the operational circuitry is configured to establish one or more parameters for P-waves associated with QRS signals including a timing relative to the QRS.

16. The IMD claim 10 wherein the operational circuitry is further configured to detect AF by monitoring for stability of the coupling interval between R-waves in the QRS signal and finding irregularly spaced R-waves.

17. The IMD of claim 10 wherein the operational circuitry is further configured, in the event that AF is not identified, to determine whether a cardiac rate of the patient exceeds a threshold and, if so, to deliver defibrillation therapy to the patient.

18. The IMD of claim 10 wherein the operational circuitry is further configured, in the event that AF is identified, to deliver cardioversion therapy to the patient to terminate the detected AF, further wherein the operational circuitry is configured to deliver the cardioversion therapy by detecting the onset of the QRS signal and delivering the cardioversion shock during a synchronized time period.

* * * * *